(12) United States Patent
Brown et al.

(10) Patent No.: US 8,742,197 B2
(45) Date of Patent: Jun. 3, 2014

(54) METHODS AND APPARATUS FOR APPLYING ADHESIVES IN PATTERNS TO AN ADVANCING SUBSTRATE

(71) Applicant: The Procter & Gamble Company, Cincinnati, OH (US)

(72) Inventors: Darrell Ian Brown, Mason, OH (US); Joseph Leslie Grolmes, Madeira, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/042,999

(22) Filed: Oct. 1, 2013

(65) Prior Publication Data

US 2014/0031777 A1    Jan. 30, 2014

Related U.S. Application Data

(63) Continuation of application No. 13/459,363, filed on Apr. 30, 2012, now Pat. No. 8,574,668, which is a continuation of application No. 13/052,139, filed on Mar. 21, 2011, now Pat. No. 8,186,296.

(60) Provisional application No. 61/331,446, filed on May 5, 2010.

(51) Int. Cl.
*A61F 13/15*    (2006.01)

(52) U.S. Cl.
USPC ..... 604/358; 604/389; 427/207.1; 427/208.2; 427/208.4

(58) Field of Classification Search
CPC . A61F 2013/1591; A61F 13/15; A61F 13/58; D21H 23/48; B05C 5/0254; B05C 5/025; B05C 11/1034

USPC .......... 427/207.1, 208.2, 208.4; 604/358, 389
See application file for complete search history.

(56) References Cited

U.S. PATENT DOCUMENTS 4,167,914 A    9/1979    Mladota
4,876,982 A    10/1989    Claassen
(Continued)

FOREIGN PATENT DOCUMENTS

EP    2 191 959 A1    6/2010
EP    1 863 594 B1    1/2011
WO    WO 2006/098934 A1    9/2006

OTHER PUBLICATIONS

PCT International Search Report dated Oct. 5, 2011, 10 pages.

*Primary Examiner* — Michael Cleveland
*Assistant Examiner* — Xiao Zhao
(74) *Attorney, Agent, or Firm* — Charles R. Matson

(57)    ABSTRACT

Methods and apparatuses herein may provide for the application of viscous fluids, such as adhesives, in pre-determined patterns to an advancing substrate. The fluid application apparatus may include a slot die applicator and a substrate carrier. The substrate carrier may include one or more pattern elements and may be adapted to advance the substrate past the slot die applicator as the slot die applicator discharges adhesive onto the substrate. In operation, the substrate is disposed on the substrate carrier; the substrate carrier advances the substrate past the slot opening of the slot die applicator. In turn, the substrate is intermittently compressed between the slot die applicator and the pattern surface of the pattern element. As the substrate is intermittently compressed, adhesive discharged from the slot die applicator is applied onto the substrate in an area having a shape substantially the same as a shape defined by the pattern surface.

9 Claims, 16 Drawing Sheets

(56) References Cited

U.S. PATENT DOCUMENTS

| | | |
|---|---|---|
| 5,168,806 A | 12/1992 | Reder et al. |
| 5,538,754 A | 7/1996 | Sandock |
| 5,759,274 A | 6/1998 | Maler et al. |
| 5,792,262 A | 8/1998 | Bohn et al. |
| 6,033,513 A | 3/2000 | Nakamura |
| 6,426,119 B1 | 7/2002 | Yapel et al. |
| 6,582,543 B1 | 6/2003 | Nilsson et al. |
| 7,056,386 B2 | 6/2006 | Pahl |
| 7,432,413 B2 | 10/2008 | Roe et al. |
| 7,444,932 B2 | 11/2008 | Strand et al. |
| 7,611,582 B2 | 11/2009 | McNeil et al. |
| 2004/0091701 A1 | 5/2004 | Toussant et al. |
| 2005/0087292 A1 | 4/2005 | McFall et al. |
| 2007/0142798 A1 | 6/2007 | Goodlander et al. |
| 2007/0287983 A1 | 12/2007 | Lodge et al. |
| 2008/0114319 A1 | 5/2008 | Burns et al. |
| 2008/0132865 A1 | 6/2008 | Li et al. |
| 2008/0221543 A1 | 9/2008 | Wilkes et al. |
| 2008/0245298 A1 | 10/2008 | Ayers |
| 2010/0252178 A1 | 10/2010 | Takino et al. |

METHODS AND APPARATUS FOR APPLYING ADHESIVES IN PATTERNS TO AN ADVANCING SUBSTRATE

CROSS REFERENCE TO RELATED APPLICATION

This application is a continuation of U.S. Ser. No. 13/459,363, filed on Apr. 30, 2012, now U.S. Pat. No. 8,574,668, which is a continuation of U.S. Ser. No. 13/052,139, filed on Mar. 21, 2011, now U.S. Pat. No. 8,186,296, which claims the benefit of U.S. Provisional Application No. 61/331,446, filed on May 5, 2010, which all are hereby incorporated by reference.

FIELD OF THE INVENTION

The present disclosure relates to methods and apparatuses utilizing continuous substrates for manufacturing articles, and more particularly, methods and apparatuses for applying viscous fluid, such as adhesives, to an advancing substrate.

BACKGROUND OF THE INVENTION

Along an assembly line, various types of articles, such as for example, diapers and other absorbent articles, may be assembled by adding components to and otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. Webs of material and component parts used to manufacture diapers may include: backsheets, topsheet, absorbent cores, front and/or back ears, fastener components, and various types of elastic webs and components such as leg elastics, barrier leg cuff elastics, and waist elastics. Once the desired component parts are assembled, the advancing web(s) and component parts are subjected to a final knife cut to separate the web(s) into discrete diapers or other absorbent articles. The discrete diapers or absorbent articles may also then be folded and packaged.

Various methods and apparatuses may be used for attaching different components to the advancing web and/or otherwise modify the advancing web. For example, some production operations are configured to apply relatively high viscosity fluids, such as hot melt adhesives, to an advancing web. In some instances, the production operations are configured to apply hot melt adhesives to an advancing web in pre-determined patterns. These operations may include the use of systems and methods such as slot die coating, direct gravure, offset gravure and reverse gravure roll coating processes that are extensively described in the art. However, current systems and methods for applying patterned adhesives to an advancing substrate may have certain limitations.

For example, in the manufacture of absorbent articles such as famine hygiene pads, baby diapers, and adult incontinence pads, the use of gravure coating processes may be confounded by contamination of the impression cylinders by fibers separated from the substrates to be coated. Some problems associated with gravure cavities and incomplete fluid transfer are described, for example, in U.S. Pat. Nos. 7,611,582 B2 and 6,003,513. In some instances, slot die coating may be used for patterned coating of webs in the manufacture of absorbent products. The use of combed shims in slot die transfer processes can provide fine resolution and precise transfer of fluid to the receiving substrate in the axis transverse to the direction of web travel. Such slot transfer processes may also be configured with electro-pneumatic switching valves to intermittently transfer adhesive to an advancing substrate. However, the quality and precision of intermittent transfer of fluids to an advancing substrate may be limited by the speed of the on/off cycle of switching valves used to interrupt the flow of fluid to the slot die of the fluid applicator. Thus, as web processing speeds increase, the ability of current slot die coating methods to achieve fine resolution of on/off coat patterns in the direction of web travel decreases.

SUMMARY OF THE INVENTION

Aspects of the present disclosure involve methods and apparatuses for applying fluids onto an advancing substrate. Particular embodiments of the apparatuses and methods disclosed herein provide for the application of viscous fluids, such as adhesives, and in some embodiments, the application of adhesives in pre-determined patterns to an advancing substrate. The fluid application apparatus may include a slot die applicator and a substrate carrier. The slot die applicator may include a slot opening, a first lip, and a second lip, the slot opening located between the first lip and the second lip. And the substrate carrier may include one or more pattern elements and may be adapted to advance the substrate past the slot die applicator as the slot die applicator discharges adhesive onto the substrate. In operation, when the first surface of the substrate is disposed on the substrate carrier, the substrate carrier advances the second surface of the substrate past the slot opening of the slot die applicator. In turn, the substrate is intermittently compressed between the slot die applicator and the pattern surface of the pattern element. As the substrate is intermittently compressed, adhesive discharged from the slot die applicator is applied onto the second surface of the advancing substrate in an area having a shape that is substantially the same as a shape defined by the pattern surface.

In one form, an apparatus for applying adhesive in a pattern to an advancing substrate, wherein the substrate having an unconstrained caliper, Hs, and having a first surface disposed opposite of a second surface, may include: a slot die applicator including a slot opening, a first lip, and a second lip, the slot opening located between the first lip and the second lip; a substrate carrier adapted to advance the substrate past the slot die applicator, wherein when the first surface of the substrate is disposed on the substrate carrier, the substrate carrier is adapted to advance the second surface of the substrate past the slot opening of the slot die applicator. The substrate carrier may include: a base surface; and a pattern element, wherein the pattern element includes a pattern surface, and wherein the pattern element protrudes outward from the base surface to define a distance, Hp, between the pattern surface and the base surface. As the substrate carrier advances the second surface of the substrate past the slot opening, the pattern element is advanced such that the pattern surface repeatedly advances past the first lip, the slot opening, and the second lip of the slot die applicator. The substrate carrier is positioned adjacent the slot die applicator to define a minimum distance, Hg, between the pattern surface of the pattern element and the first lip and the second lip that is less than the unconstrained caliper, Hs, of the substrate, wherein a sum of the distance, Hp, and distance, Hg, is greater than the unconstrained caliper, Hs, of the substrate.

In another form, an apparatus for applying adhesive in a pattern to an advancing substrate, the substrate having an unconstrained caliper, Hs, and having a first surface disposed opposite of a second surface, may include: a slot die applicator including a slot opening, a first lip, and a second lip, the slot opening located between the first lip and the second lip; a substrate carrier adapted to advance the substrate past the slot die applicator, wherein when the first surface of the substrate is disposed on the substrate carrier, the substrate carrier is adapted to advance the second surface of the substrate past the slot opening of the slot die applicator. The substrate carrier may include: a pattern element, wherein the pattern surface comprises a continuous pattern surface; and a plurality of holes separated from each other by the pattern element. As the substrate carrier advances the second surface of the substrate past the slot opening, the pattern element is advanced such that the pattern surface repeatedly advances past the first lip, the slot opening, and the second lip of the slot die applicator. The substrate carrier is positioned adjacent the slot die applicator to define a minimum distance, Hg, between the pattern surface of the pattern element and the first lip and the second lip that is less than the unconstrained caliper, Hs, of the substrate.

In yet another form, a method may apply adhesive discharged from a slot die applicator to a substrate in a pattern, wherein the slot die applicator includes a slot opening, a first lip, and a second lip, the slot opening located between the first lip and the second lip; and the substrate includes a first surface disposed opposite of a second surface and an unconstrained caliper, Hs. The method may include the steps of: continuously advancing the substrate in a machine direction; engaging the substrate with a substrate carrier, the substrate carrier comprising: a pattern element, wherein the pattern element includes an pattern surface; positioning the substrate carrier adjacent the slot die applicator to define a minimum distance, Hg, between the pattern surface of the pattern element and the first lip and the second lip that is less than the unconstrained caliper, Hs, of the substrate; advancing the second surface of the substrate past the slot die applicator while the first surface of the substrate is disposed on the substrate carrier; intermittently compressing the substrate between the slot die applicator and the pattern surface of the pattern element by advancing the pattern element such that the pattern surface of the pattern element advances past the first lip, the slot opening, and the second lip of the slot die applicator while the first surface of the substrate is disposed on the substrate carrier; and discharging adhesive from the slot opening of the slot die applicator onto the second surface of the substrate.

DETAILED DESCRIPTION OF THE INVENTION

Figure 1:
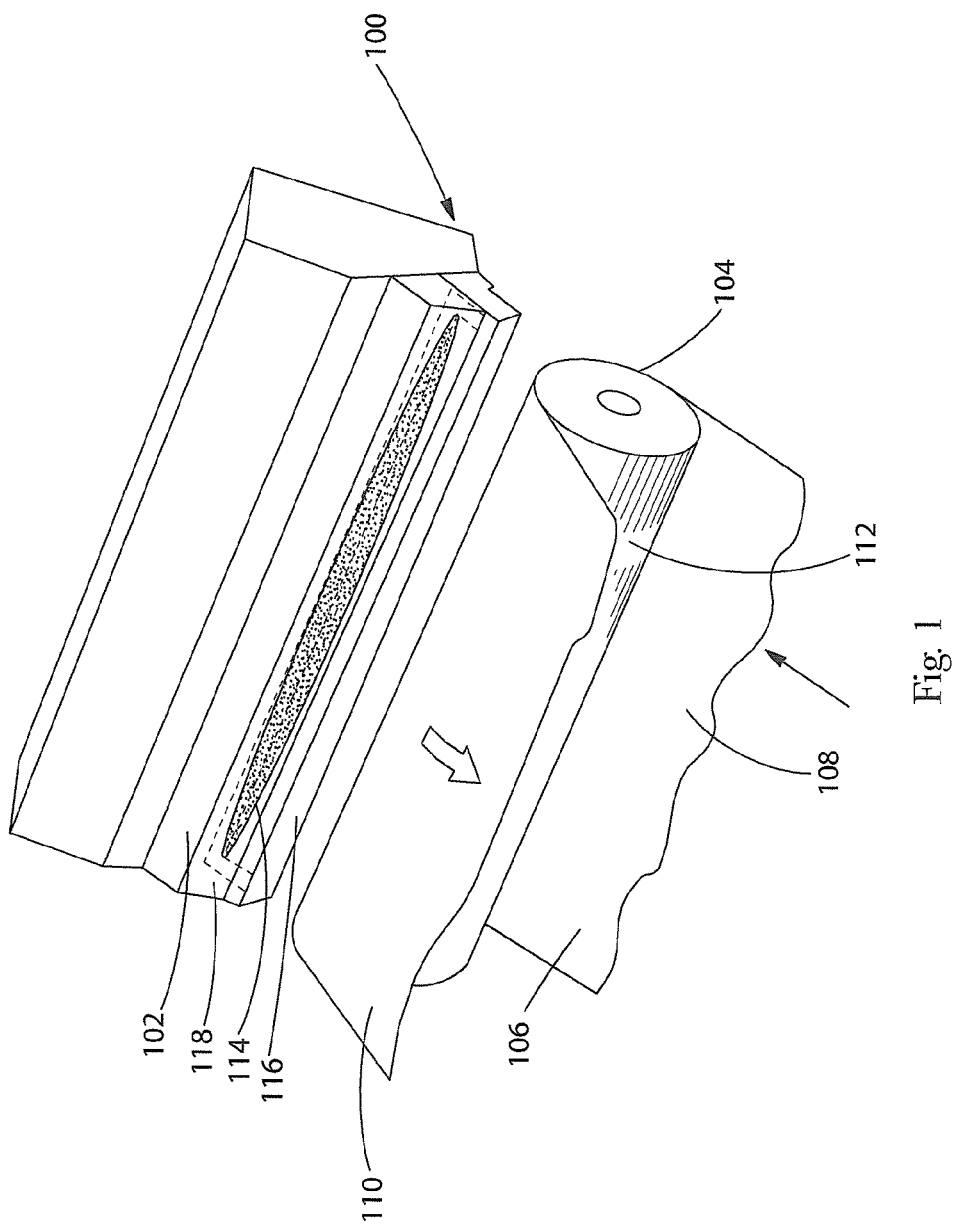
FIG. 1 is a perspective view of a fluid application apparatus positioned adjacent to an advancing substrate.

The following term explanations may be useful in understanding the present disclosure:

"Absorbent article" is used herein to refer to consumer products whose primary function is to absorb and retain soils and wastes. Non-limiting examples of absorbent articles include diapers, training pants, pull-on pant-type diapers, refastenable diapers or pant-type diapers, incontinence briefs and undergarments, diaper holders and liners, feminine hygiene garments such as panty liners, absorbent inserts, and the like.

"Diaper" is used herein to refer to an absorbent article generally worn by infants and incontinent persons about the lower torso.

The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "disposed" is used herein to mean that an element (s) is formed (joined and positioned) in a particular place or position as a macro-unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a layer or layers or fibrous materials, films and foils such as plastic films or metallic foils that may be used alone or laminated to one or more web, layer, film and/or foil. As such, a web is a substrate.

The term "nonwoven" refers herein to a material made from continuous (long) filaments (fibers) and/or discontinuous (short) filaments (fibers) by processes such as spunbonding, meltblowing, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The terms "elastic" and "elastomeric" as used herein refer to any material that upon application of a biasing force, can stretch to an elongated length of at least about 110% of its relaxed, original length (i.e. can stretch to 10% more than its original length), without rupture or breakage, and upon release of the applied force, recovers at least about 40% of its elongation. For example, a material that has an initial length of 100 mm can extend at least to 110 mm, and upon removal of the force would retract to a length of 106 mm (40% recovery). The term "inelastic" refers herein to any material that does not fall within the definition of "elastic" above. The term "extensible" as used herein refers to any material that upon application of a biasing force, can stretch to an elongated length of at least about 110% of its relaxed, original length (i.e. can stretch to 10%), without rupture or breakage, and upon release of the applied force, shows little recovery, less than about 40% of its elongation.

The terms "activating", "activation" or "mechanical activation" refer to the process of making a substrate, or an elastomeric laminate more extensible than it was prior to the process.

"Live Stretch" includes stretching elastic and bonding the stretched elastic to a substrate. After bonding, the stretched elastic is released causing it to contract, resulting in a "corrugated" substrate. The corrugated substrate can stretch as the corrugated portion is pulled to about the point that the substrate reaches at least one original flat dimension. However, if the substrate is also elastic, then the substrate can stretch beyond the relaxed length of the substrate prior to bonding with the elastic. The elastic is stretched at least 25% of its relaxed length when it is bonded to the substrate.

As used herein, the term "unconstrained caliper" refers to the caliper of the substrate measured according to Edana WSP 120.1 (05), with a circular presser foot having a diameter of 25.40±0.02 mm and an applied force of 2.1 N (i.e. a pressure of 4.14±0.21 kPa is applied).

Aspects of the present disclosure involve methods and apparatuses utilizing continuous substrates for manufacturing articles, and more particularly, methods and apparatuses for applying fluids onto an advancing substrate. Particular embodiments of the apparatuses and methods disclosed herein provide for the application of viscous fluids, such as adhesives, and in some embodiments, the application of adhesives in pre-determined patterns to an advancing substrate. Embodiments of a fluid application apparatus are discussed in more detail below in the context of applying adhesives to an advancing substrate having an unconstrained caliper, Hs, and having a first surface disposed opposite of a second surface. The fluid application apparatus may include a slot die applicator and a substrate carrier. The slot die applicator may include a slot opening, a first lip, and a second lip, the slot opening located between the first lip and the second lip. And the substrate carrier may be adapted to advance the substrate past the slot die applicator as the slot die applicator discharges adhesive onto the substrate. In operation, when the first surface of the substrate is disposed on the substrate carrier, the substrate carrier advances the second surface of the substrate past the slot opening of the slot die applicator. It is to be appreciated that the apparatus and processes disclosed herein may be used to apply various types of fluids and adhesives in various different patterns to an advancing substrate other than those described and depicted herein.

As discussed in more detail below, the substrate carrier may include a base surface and a pattern element. In some embodiments, the substrate carrier may include a plurality of holes therein, and as such, do not include base surfaces. The pattern element includes a pattern surface and protrudes outward from the base surface. As such, in substrate carriers configured with a base surface, the pattern surface and the base surface are separated by a distance, Hp. In addition, the substrate carrier is positioned adjacent the slot die applicator to define a minimum distance, Hg, between the pattern surface of the pattern element and the first lip and the second lip that is less than the unconstrained caliper, Hs, of the substrate, wherein a sum of the distance, Hp, and distance, Hg, is greater than the unconstrained caliper, Hs, of the substrate. Thus, as the substrate carrier advances the second surface of the substrate past the slot opening, the pattern element is advanced such that the pattern surface repeatedly advances past the first lip, the slot opening, and the second lip of the slot die applicator. In turn, the substrate is intermittently compressed between the slot die applicator and the pattern surface of the pattern element as the pattern element advances past the first lip, the slot opening, and the second lip of the slot die applicator. As the substrate is intermittently compressed, adhesive discharged from the slot die applicator is applied onto the second surface of the advancing substrate. More particularly, the adhesive is applied to the substrate in an area having a shape that is substantially the same as a shape defined by the pattern surface.

The apparatuses and methods disclosed herein may include substrate carriers having various configurations. For example, in some embodiments the substrate carrier may be configured as a roller. In other embodiments, the substrate carrier may include an endless belt. The substrate carriers may also utilize various outer surface arrangements. For example, the base surface may be configured as a continuous surface and the substrate carrier may include a plurality of discrete pattern elements separated from each other by the continuous surface. In such a configuration, each pattern element may include a pattern surface and each pattern element may protrude outward from the continuous surface such that each pattern surface is separated from the continuous surface by the distance, Hp. In another example, the pattern surface may be configured as a continuous surface and the base surface may include a plurality of discrete base surfaces separated from each other by the pattern element. In such a configuration, the pattern element may protrude outward from each of the base surfaces such that each base surface is separated from the continuous surface by the distance, Hp. As previously mentioned, in some configurations, the substrate carrier may be configured without base surfaces, such as for example, a belt configured with holes extending through the belt. As such, the holes may be separated from each other by a continuous pattern element. It is to be appreciated that the pattern surface of the pattern element may be configured in various different shapes and sizes and may be configured to define various different patterns. As such, adhesive may be transferred from the slot die applicator to define various patterns on a substrate.

As mentioned above, apparatuses and methods of the present disclosure may be utilized to apply adhesives to continuous substrates used in the manufacture of absorbent articles. Such substrates may be utilized in absorbent article components such as, for example: backsheets, topsheets, absorbent cores, front and/or back ears, fastener components, and various types of elastic webs and components such as leg elastics, barrier leg cuff elastics, and waist elastics. Exemplary descriptions of absorbent article components and substrates are provided below with reference to FIG. 9. In addition, substrates may include continuous webs of material and component parts mounted on carrier substrates or may be in the form of a continuous substrate.

Although much of the present disclosure is provided in the context of manufacturing absorbent articles, it is to be appreciated that the apparatuses and methods disclosed herein may be applied to the manufacture of other types of articles and products manufactured from continuous substrates. Examples of other products include absorbent articles for inanimate surfaces such as consumer products whose primary function is to absorb and retain soils and wastes that may be solid or liquid and which are removed from inanimate surfaces such as floors, objects, furniture and the like. Non-limiting examples of absorbent articles for inanimate surfaces include dusting sheets, pre-moistened wipes or pads, pre-moistened cloths, paper towels, dryer sheets and dry-cleaning clothes such. Additional examples of products include absorbent articles for animate surfaces whose primary function is to absorb and contain body exudates and, more specifically, devices which are placed against or in proximity to the body of the user to absorb and contain the various exudates discharged from the body. Non-limiting examples of incontinent absorbent articles include diapers, training and pull-on pants, adult incontinence briefs and undergarments, feminine hygiene garments such as panty liners, absorbent inserts, and the like, toilet paper, tissue paper, facial wipes or clothes, and toilet training wipes. Still other examples of products may include packaging components and substrates and/or containers for laundry detergent and coffee, which may be produced in pellets or pouches and may be manufactured in a converting or web process or even discreet products produced at high speed such as high-speed bottling lines, cosmetics, razor blade cartridges, and disposable consumer batteries.

FIG. 1 shows a perspective view an embodiment of an apparatus 100 for applying adhesives to a substrate. The apparatus 100 includes a slot die applicator 102 and a substrate carrier 104. As shown in FIG. 1, a substrate 106 is advancing in a machine direction and is partially wrapped around the substrate carrier 104. More particularly, the substrate 106 includes a first surface 108 disposed opposite a second surface 110. And the first surface 108 of the substrate 106 is disposed on an outer surface 112 of the substrate carrier 104 while the second surface 110 of the substrate 106 advances past the slot die applicator 104. As discussed in more detail below, the second surface 110 of the substrate 106 advances past the slot die applicator 104 and adhesive is transferred from the slot die applicator 102 onto the second surface of the substrate in a pattern that is substantially the same as a pattern defined on the outer surface 112 of the substrate carrier 104.

It is to be appreciated that the slot die applicator 102 shown in FIG. 1 is a generic representation of a device that is used to apply adhesive to the substrate 106. The slot die applicator may include a slot opening 114, a first lip 116, and a second lip 118. The first lip 116 may also be referred to herein as an upstream die lip, and the second lip 118 may also be referred to herein as a downstream die lip. The slot opening 114 is located between the first lip 116 and the second lip 118. Adhesive or other fluid may be discharged from the slot opening 114 onto the second surface 110 of the substrate 106 as the substrate carrier 104 advances the substrate past the first lip 116, slot opening 114, and second lip 118 of the slot die applicator 102. As discussed in more detail below, the substrate 106 is also intermittently compressed between the slot die applicator 102 and substrate carrier 104 as the substrate 106 advances past the slot die applicator 102. It is to be appreciated that various forms of slot die applicators may be used herein to apply adhesive or other fluids to an advancing substrate according to methods and apparatuses. For example, U.S. Pat. No. 7,056,386 provides a description of slot die applicators that may be used. Other examples of commercially available slot die applicators include Nordson Corporation's EP11 Series of Slot Die Applicators and ITW Dynatec Gmbh's APEX Series of Slot Die Auto Adhesive Applicators.

Figure 2A:
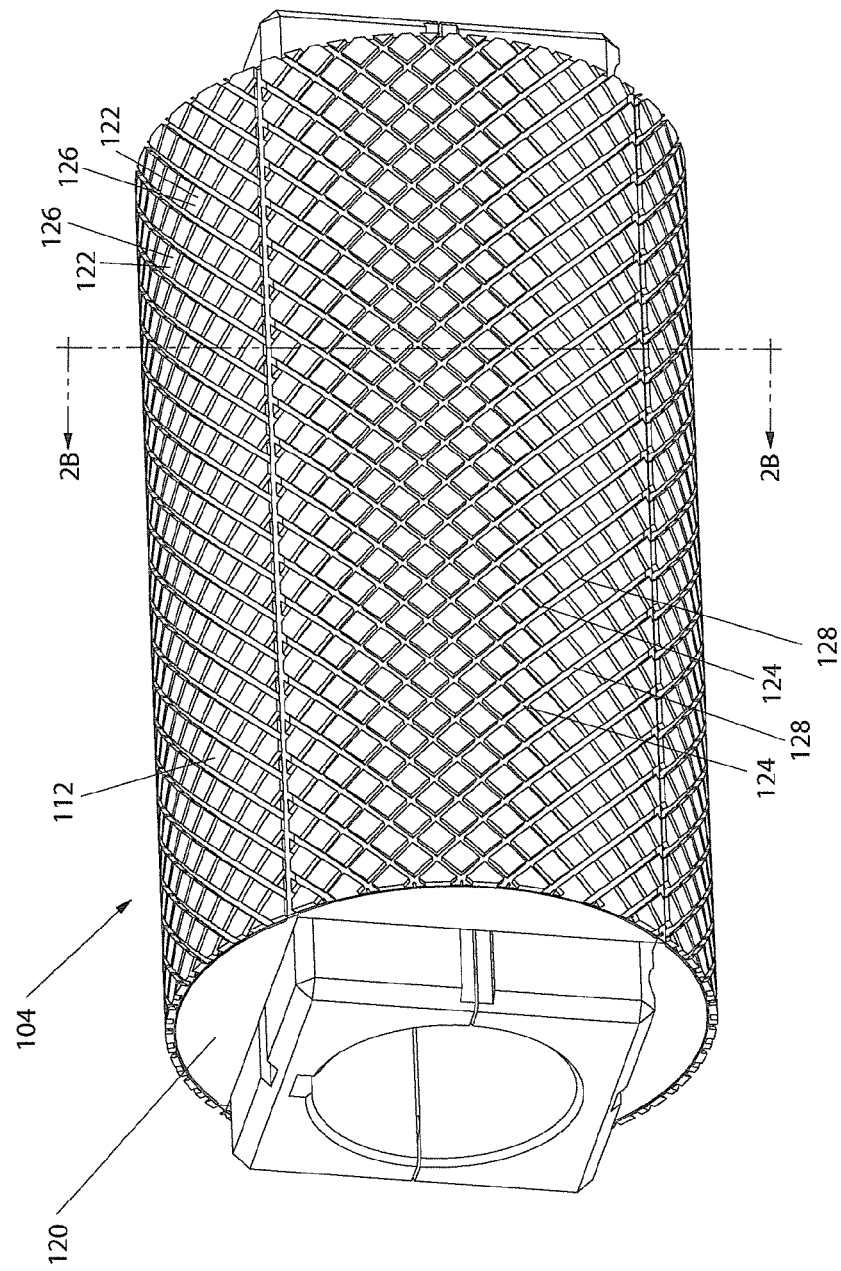
FIG. 2A is a perspective view of an embodiment of a substrate carrier including a pattern roller having a continuous base surface and a plurality of pattern surfaces.
Figure 2B:
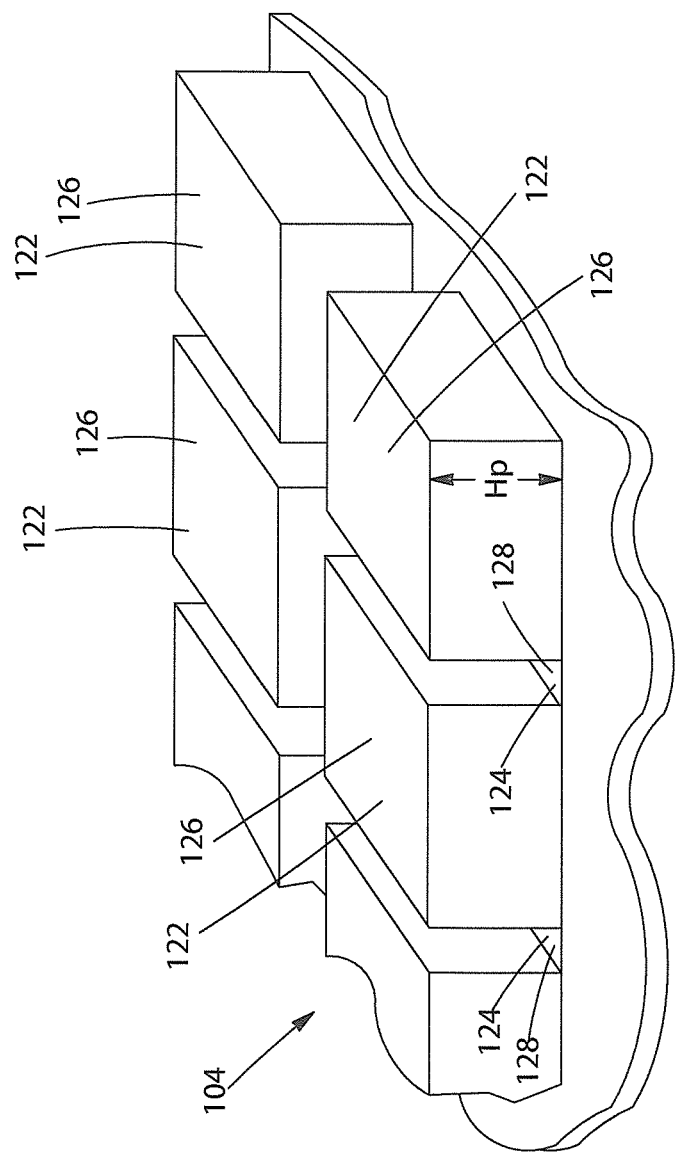
FIG. 2B is a detailed cross-sectional view of the substrate carrier shown in FIG. 2A taken along the line 2B-2B.

Various types of substrate carriers 104 may be used in accordance with the apparatuses and methods herein. For example, FIGS. 2A and 2B show an embodiment of a substrate carrier 104 configured as a roller 120 adapted to advance a substrate 106 past the slot die applicator 102. The outer surface 112 of the substrate carrier 104 shown in FIGS. 2A and 2B includes a plurality of pattern elements 122 that protrude radially outward from a base surface 124. Each pattern element 122 includes a pattern surface 126, and the radial protrusion of the pattern elements 122 from the base surface 124 define a distance, Hp, between the pattern surface 126 and the base surface 124. As shown in FIGS. 2A and 2B, the base surface 124 is configured as a continuous surface 128, and the plurality of discrete pattern elements 122 are separated from each other by the continuous surface 128. The pattern surfaces 126 in FIGS. 2A and 2B define a diamond shape. In some embodiments, the shape and size of the pattern surface 126 of each pattern element 122 may be identical or substantially identical to each other. It is to be appreciated that the number, size, and shape of some or all the pattern surfaces and/or pattern elements may be different. In addition, the distance, Hp, between the base surface 124 and the pattern surface 126 of the pattern element 122 may be the same or different for some or all of the pattern elements.

Figure 2C:
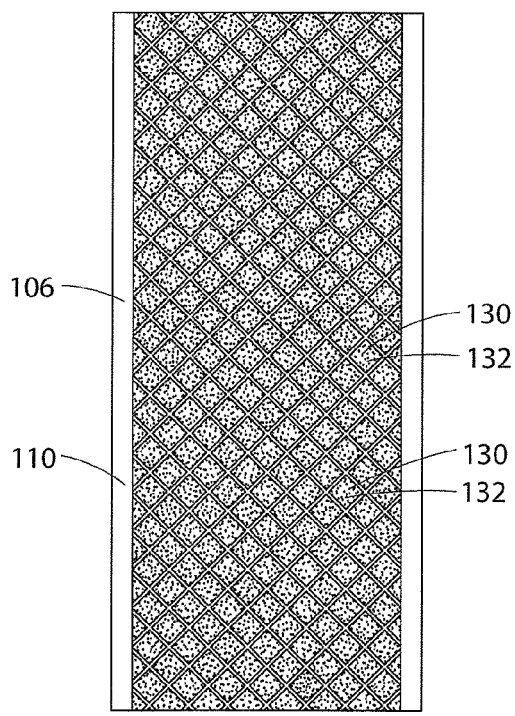
FIG. 2C is a top side view of a substrate showing a first example adhesive pattern thereon.

As discussed in more detail below, as the substrate carrier 104 advances the substrate 106 past the slot die applicator 102, fluid discharged from the slot die applicator is deposited onto the substrate in a pattern substantially matching the shapes of the pattern surfaces on the substrate carrier. For example, FIG. 2C shows an example pattern of fluid 130 deposited on a second surface 110 of a substrate 106 after being advanced past a slot die applicator while disposed on a substrate carrier having pattern elements 122 and pattern surfaces 126 similar to those shown in FIGS. 2A and 2B. As shown in FIG. 2C, the fluid 130 is deposited onto the substrate 106 in discrete pattern areas 132 having diamond shapes that correspond with the shapes of the pattern surfaces 126 on the substrate carrier 104 shown in FIG. 2A.

Figure 3C:
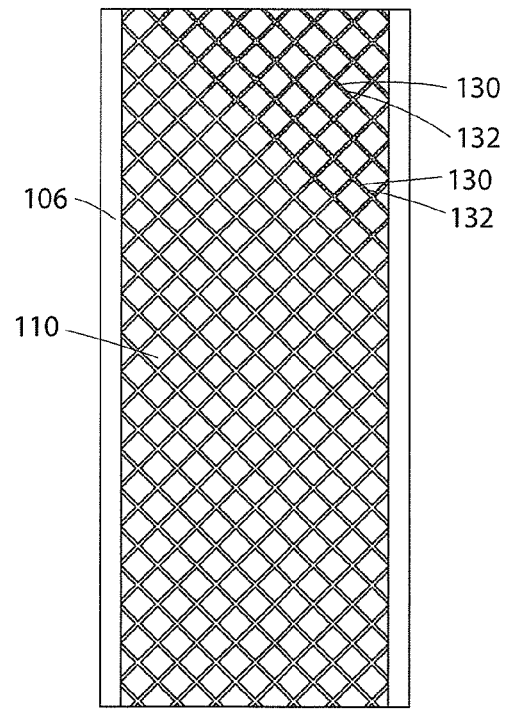
FIG. 3C is a top side view of a substrate showing a second example adhesive pattern thereon.
Figure 3A:
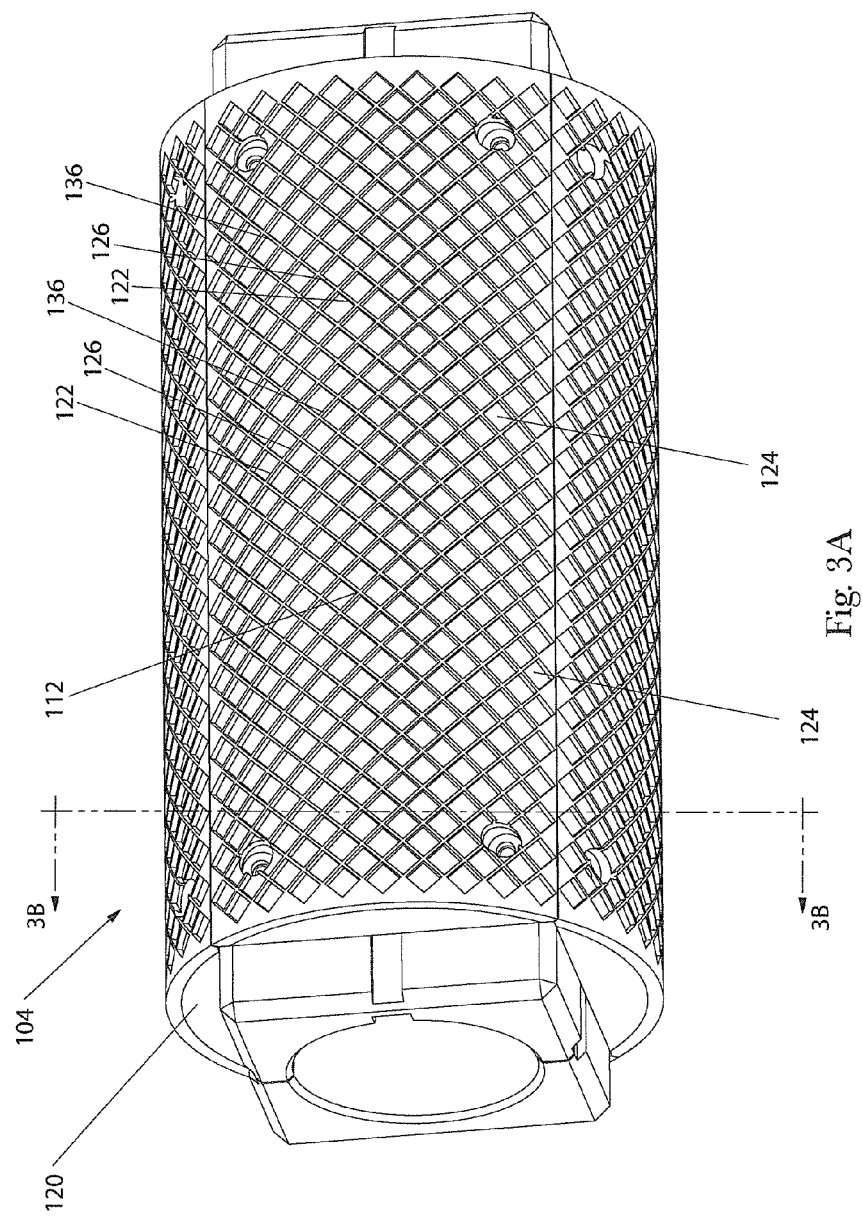
FIG. 3A is a perspective view of an embodiment of a substrate carrier including a pattern roller having a continuous pattern surface and plurality of base surfaces.
Figure 3B:
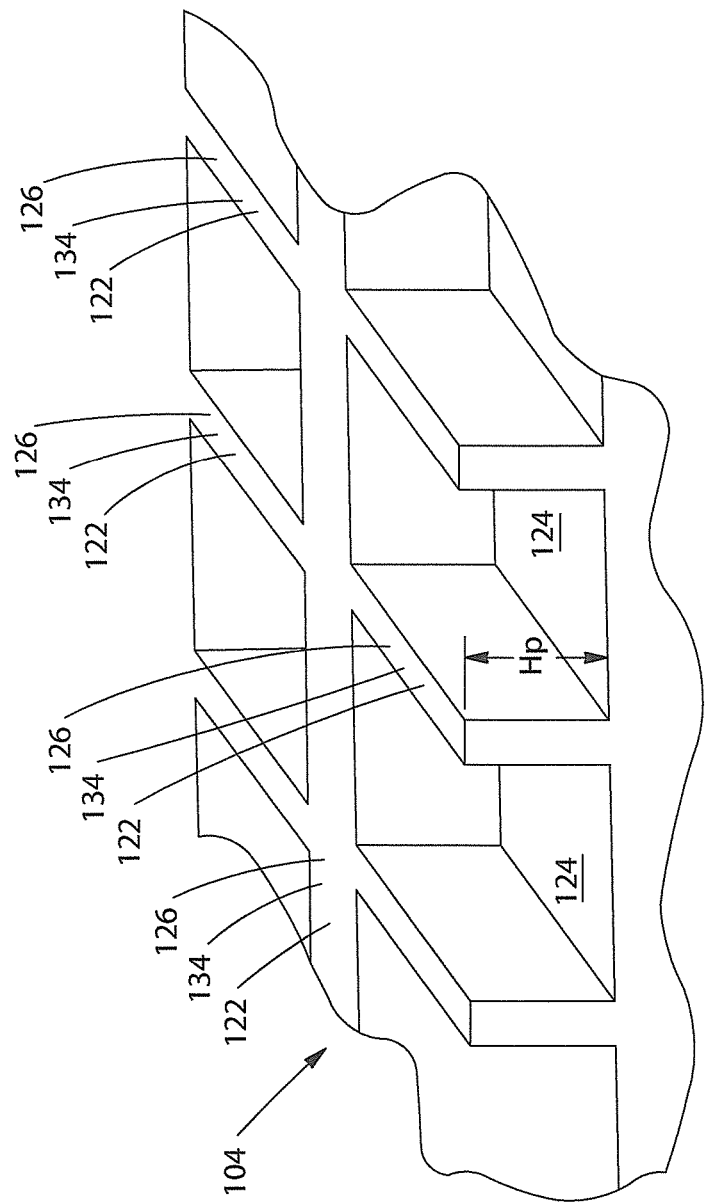
FIG. 3B is a detailed cross-sectional view of the substrate carrier shown in FIG. 3A taken along the line 3B-3B.
Figure 3D:
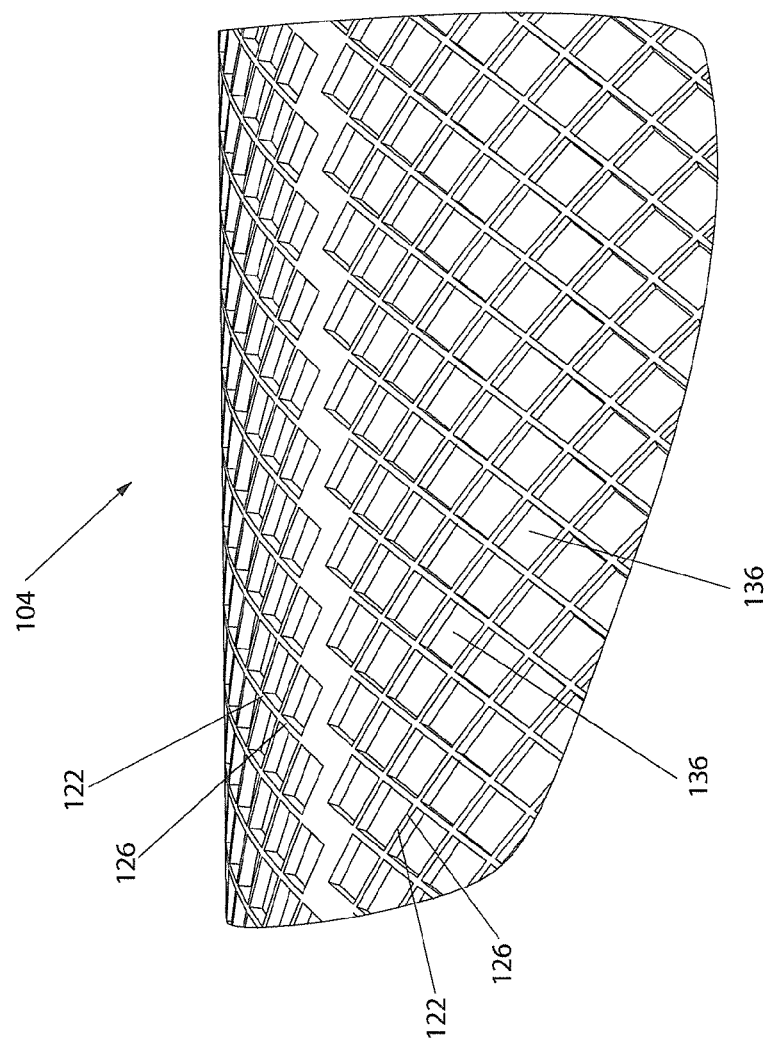
FIG. 3D is a detailed cut-away view of a substrate carrier including a continuous pattern surface and a plurality of holes.

FIGS. 3A and 3B show another embodiment of a substrate carrier 104 configured as a roller 120 adapted to advance a substrate 106 past the slot die applicator 102. The substrate carrier 104 shown in FIGS. 3A and 3B includes a single pattern element 122 including a pattern surface 126. And the pattern element 122 protrudes radially outward from a plurality of base surfaces 124. More particularly, the pattern surface 126 is configured as a continuous surface 134 and the plurality of base surfaces are separated from each other by the pattern element 122. The radial protrusion of the pattern element 122 from the base surfaces 124 defines a distance, Hp, between the pattern surface 126 and the base surfaces 124. The pattern surface 126 in FIGS. 3A and 3B defines a continuous crossing line pattern wherein the shape and size of each base surface 124 are identical or substantially identical to each other. It is to be appreciated that the number, size, and shape of some or all the base surfaces may be different. In addition, the distance, Hp, between the base surfaces 124 and the pattern surface 126 of the pattern element 122 may be the same or different for some or all of the base surfaces. It should also be appreciated that the substrate carrier may be configured without base surfaces. For example, the substrate carrier may include a plurality of holes and the pattern surface may be configured as a continuous surface wherein the plurality of holes are separated from each other by the pattern element. For example, FIG. 3D shows a detailed view of a substrate carrier embodiment wherein a plurality of holes 136 are separated from each other by a pattern element 122 having a continuous pattern surface 126. Because the substrate carrier 104 of FIG. 3D does not have base surfaces, a distance, Hp, is not defined.

As previously mentioned, as the substrate carrier 104 advances the substrate 106 past the slot die applicator 102, fluid 130 discharged from the slot die applicator 102 is deposited onto the substrate 106 in a pattern substantially matching the shape of the pattern surface 126 on the substrate carrier 104. For example, FIG. 3C shows an example pattern of fluid 130 deposited on a second surface 110 of a substrate 106 after being advanced past a slot die applicator 102 while disposed on a substrate carrier 104 having a pattern element 122 and pattern surface 126 similar to that shown in FIGS. 3A, 3B, and 3D. As shown in FIG. 3C, the fluid 130 is deposited onto the substrate 106 in a crossing line pattern defining diamond shapes therebetween that correspond with the shapes of the base surfaces 124 and holes 136 on the substrate carrier 104 shown in FIGS. 3A and 3D, respectively.

Figure 4:
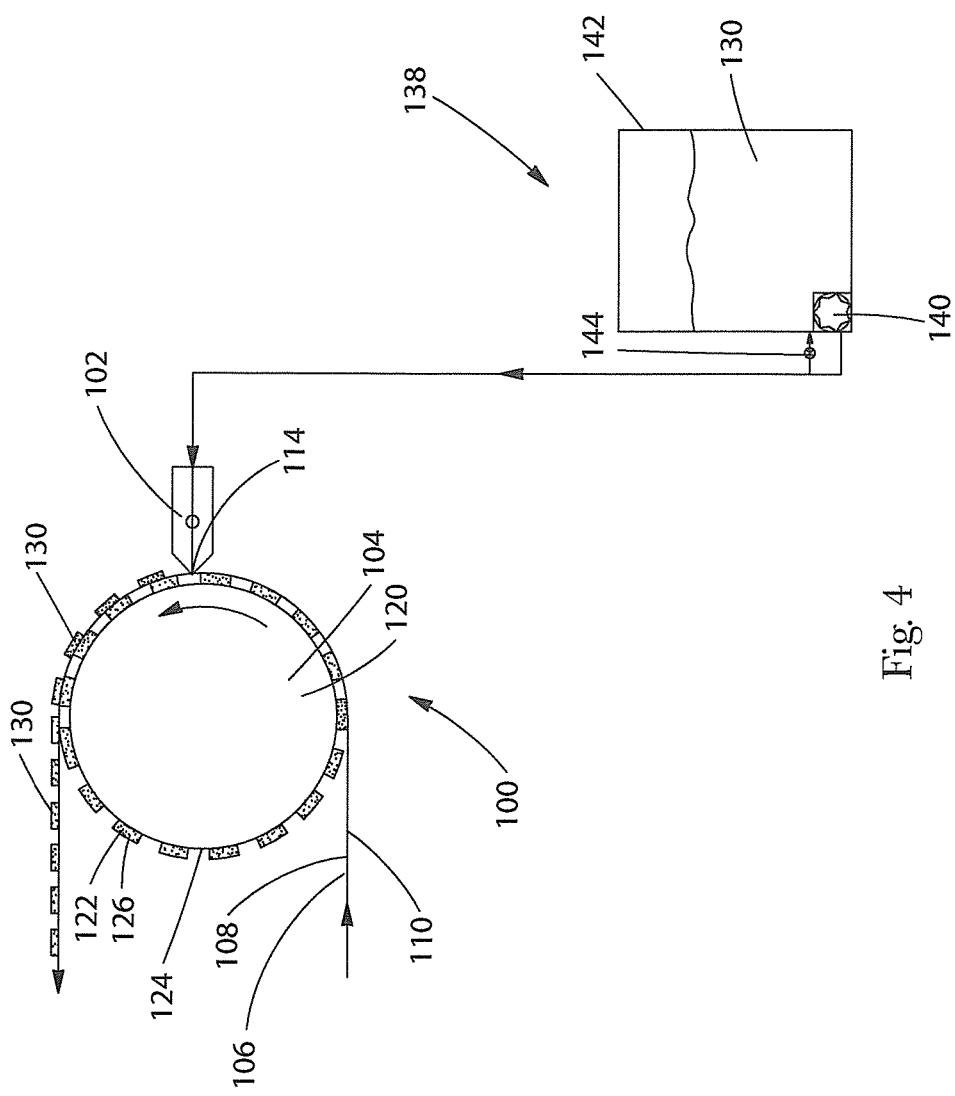
FIG. 4 is a schematic cross-sectional side view of a fluid application apparatus.

As previously mentioned, the methods and apparatuses herein include a substrate carrier adapted to advance a substrate past a slot die applicator. FIG. 4 shows a schematic cross-sectional side view of an embodiment of a fluid application apparatus 100 including a substrate carrier 104 and a slot die applicator 102. The substrate 106 includes a first surface 108 and a second surface 110 disposed opposite the first surface 108. A portion of the first surface 108 of the substrate 106 is disposed on the substrate carrier 104, which is configured as a roller 120 having a plurality of pattern elements 122 protruding from a plurality of base surfaces 124. The roller 120 rotates to advance the second surface 110 of the substrate 106 past the slot die applicator 102. A fluid delivery system 138 may be used to supply fluid 130, such as an adhesive, to the slot die applicator 102. It is to be appreciated that the fluid delivery system may be configured in various different ways. For example, as shown in FIG. 4, the fluid delivery system 138 may include a pump 140 to move fluid from a tank 142 to the slot die applicator 102. The fluid delivery system 138 may also be configured with a pressure relief valve 144 configured to help control the pressure of the fluid 130 fed from the pump 140. Fluid 130 from the fluid delivery system 138 passes through the slot die applicator 102 and slot opening 114 and is transferred to the second surface 110 of the advancing substrate 106.

With continued reference to FIG. 4, fluid 130 passing from the slot die applicator 102 is transferred to the second surface 110 of the substrate 106 in a pattern or shape that is substantially the same as the pattern surfaces 126 on the substrate carrier 104. As discussed in more detail below, the substrate carrier 104 is positioned adjacent the slot die applicator 102 to define a minimum distance between the pattern surface 126 and slot die applicator 102, which is less than the unconstrained caliper of the substrate 106. As such, the substrate 106 is compressed between the slot die applicator 102 and the pattern surface 126 of the pattern element 122 as the pattern element advances past the first lip 116, the slot opening 114, and the second lip 118 of the slot die applicator 102. However, the minimum distance between the base surface 124 of the substrate carrier 104 and the slot die applicator 102 is greater than the unconstrained caliper of the substrate 106. As such, the substrate 106 is not compressed between the slot die applicator 102 and the base surface 124 as the substrate advances past the first lip 116, the slot opening 114, and the second lip 118 of the slot die applicator 102. Thus, in operation, although fluid 130 is continuously discharged from the slot die applicator 102, fluid 130 is transferred to the advancing substrate 106 when the substrate is compressed as pattern surfaces 126 on the substrate carrier 102 advance past the slot die opening 114 and compress the substrate. And fluid 130 is not transferred to the advancing substrate 106 when the substrate is uncompressed while base surfaces 124 on the substrate carrier 104 advance past the slot die opening 114. With regard to substrate carriers configured with holes 136, as opposed to base surfaces, fluid 130 is not transferred to the advancing substrate 106 when the substrate is uncompressed while holes 136 on the substrate carrier 104 advance past the slot die opening 114. The following provides a more detailed description of fluid transfer from the slot die applicator to the substrate with reference to FIGS. 5A through 5D.

Figure 5A:
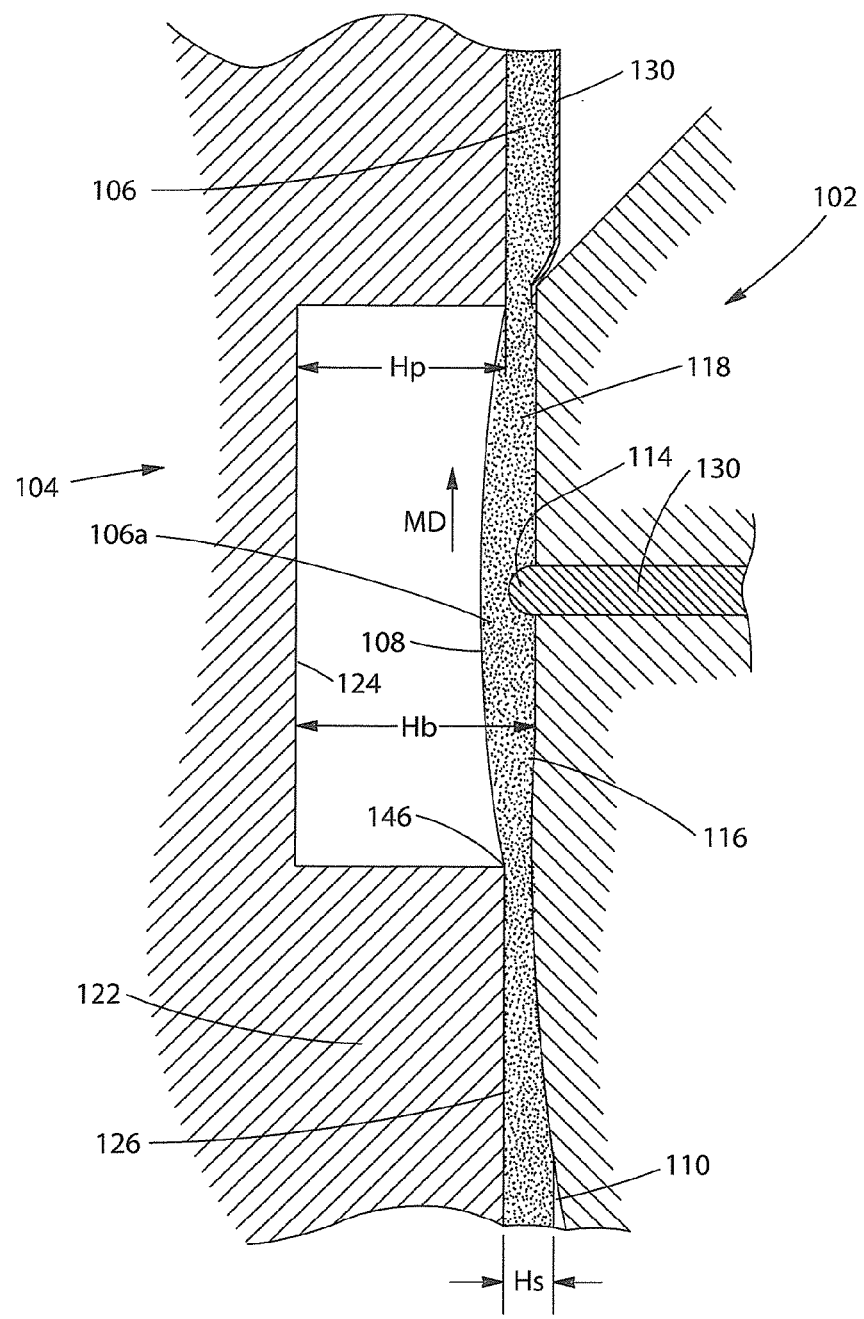
FIG. 5A is a detailed cross-sectional view of a substrate carrier and a substrate advancing past a slot die applicator and showing the substrate between a slot opening of the slot die applicator and an advancing base surface.

FIG. 5A is a detailed cross-sectional view of a substrate carrier 104 and a substrate 106 advancing past a slot die applicator 102. The substrate 106 has an unconstrained caliper, Hs, and has a first surface 108 disposed opposite of a second surface 110. The first surface 108 of the substrate 106 is disposed on the substrate carrier 104. And the substrate 106 and substrate carrier 104 are shown as advancing together in a machine direction, MD, past the slot die applicator 102. More particularly, the second surface 110 of the substrate 106 is advancing past a slot opening 114 located between an upstream lip 116 and a downstream lip 118 of the slot die applicator 104.

As shown in FIG. 5A, the substrate carrier 104 includes a base surface 124 and a pattern element 122 protruding from base surface 124. The pattern element 122 protrudes outward from the base surface 124 to define a distance, Hp, between the pattern surface 126 and the base surface 124. The substrate carrier 104 is also positioned adjacent the slot die applicator 104 to define a minimum distance, Hg, between the pattern surface 124 of the pattern element 122 and the first lip 116 and the second lip 118 that is less than the unconstrained caliper, Hs, of the substrate 106. In addition, the substrate carrier 104 is positioned adjacent the slot die applicator 102 to define a minimum distance, Hb, between the base surface 124 and the first lip 116 and the second lip 118 that is greater than the unconstrained caliper, Hs, of the substrate. The apparatus 100 may also be configured such that a sum of the distance, Hp, and distance, Hg, is greater than the unconstrained caliper, Hs, of the substrate 106. Thus, a portion 106a of the substrate 106 that is located between the slot opening 114 of the slot die applicator 104 and the advancing base surface 124 is not compressed. As such, although fluid 130 is continuously discharged from the slot opening 114, fluid 130 is not being transferred to the second surface 110 of the substrate 104.

Figure 5B:
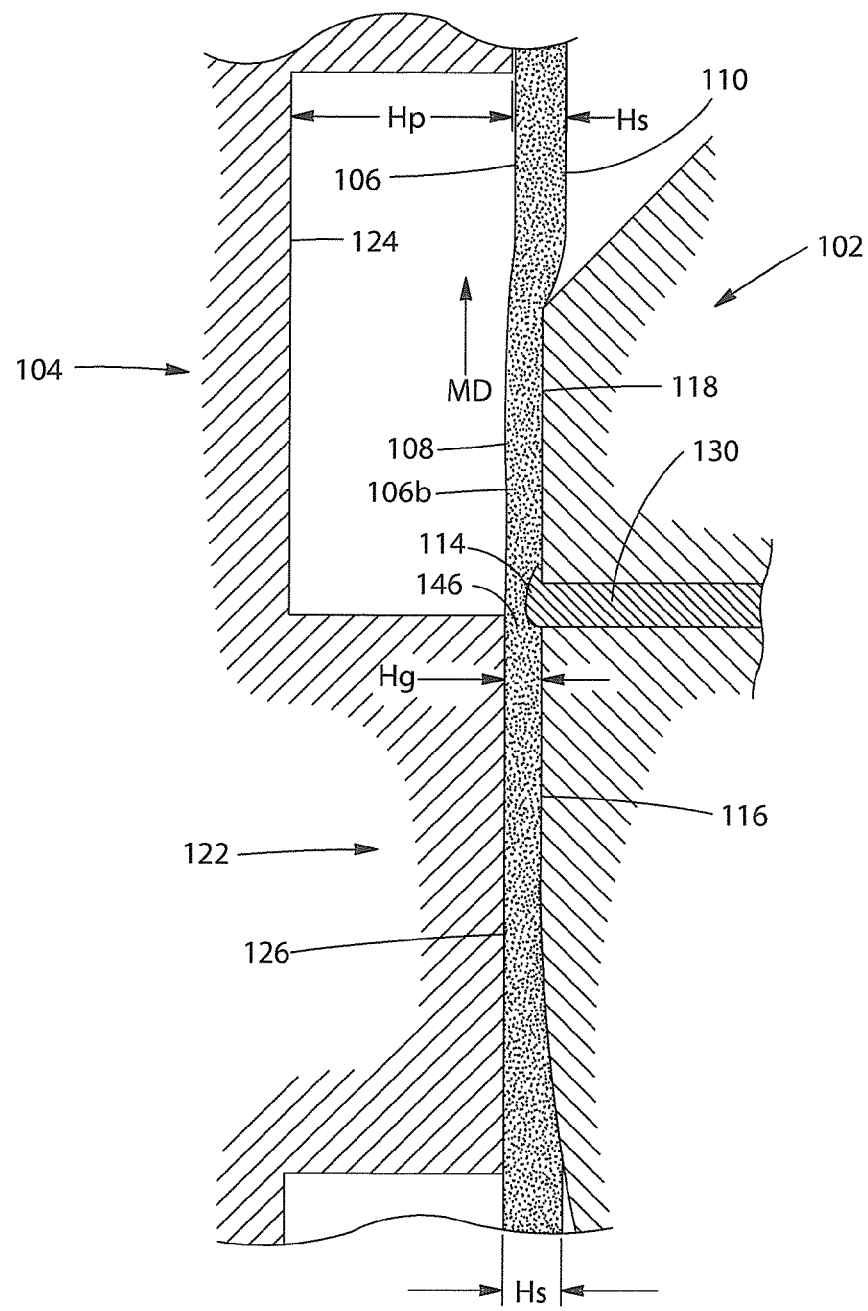
FIG. 5B is a detailed cross-sectional view of the substrate carrier and substrate of FIG. 5A wherein the base surface is advancing past the slot opening of the slot die applicator such the substrate is between the slot opening of the slot die applicator and a leading edge of an advancing pattern surface.

FIG. 5B is a detailed cross-sectional view of the substrate carrier 104 and substrate 106 of FIG. 5A wherein the base surface 124 has advanced past the slot opening 114 of the slot die applicator 104 such that a portion 106b of the substrate 106 is between the first lip 116 of the slot die applicator 104 and a leading edge 146 of an advancing pattern surface 126. As previously discussed, the minimum distance, Hg, between the pattern surface 126 of the pattern element 122 and the first lip 116 and the second lip 118 is less than the unconstrained caliper, Hs, of the substrate 106. As such, a portion 106b of substrate 106 between the pattern surface 126 and the first lip 116 is compressed. The fluid 130 being discharged from the slot opening 114 is shown in FIG. 5B as beginning to transfer to the second surface 110 of the substrate as the leading edge 146 of the pattern surface 126 and adjacent compressed portion 106b of the substrate 106 begin to advance past the slot opening 114.

Figure 5C:
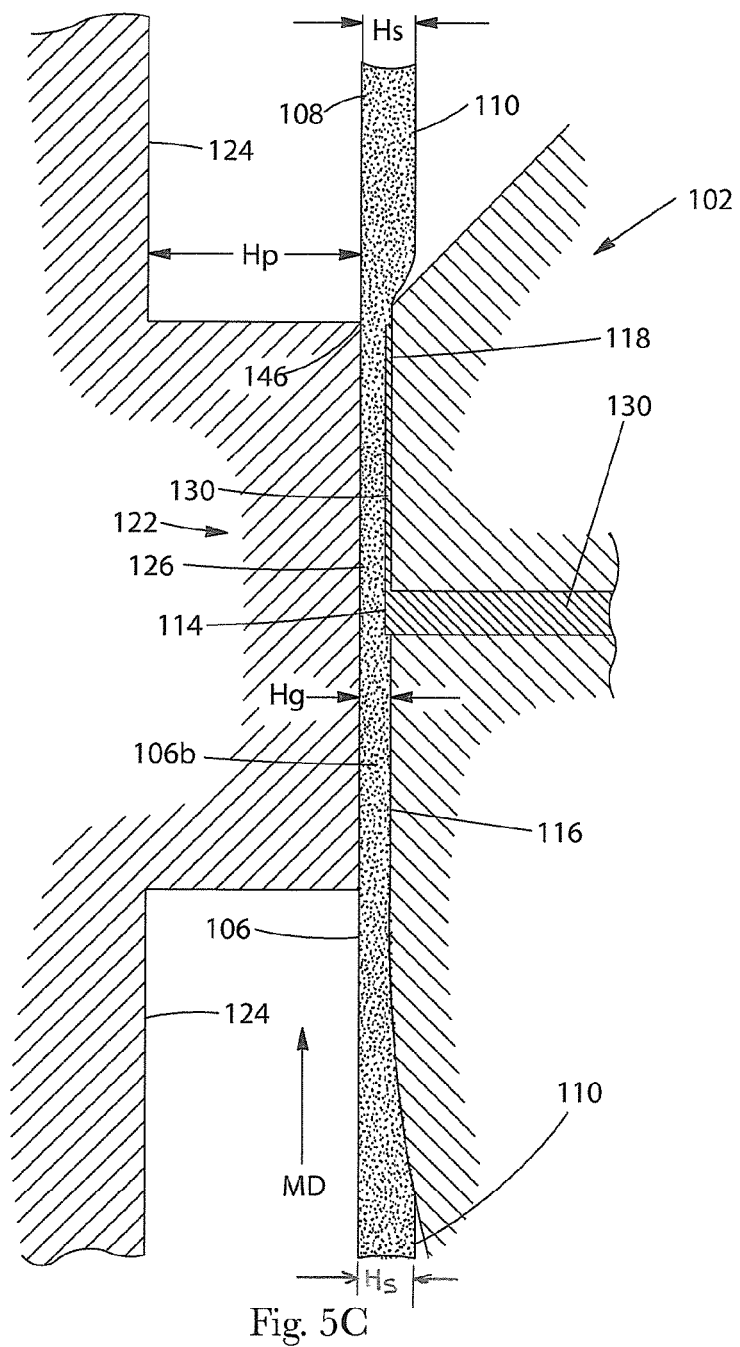
FIG. 5C is a detailed cross-sectional view of the substrate carrier and substrate of FIG. 5B wherein the base surface has advanced past the slot opening of the slot die applicator such that the substrate is between the slot opening of the slot die applicator and an advancing pattern surface.

FIG. 5C is a detailed cross-sectional view of the substrate carrier 104 and substrate of FIG. 5B wherein the base surface 124 and leading edge 146 of the pattern surface 126 has advanced past the slot opening 114 of the slot die applicator 104 such that a portion 106b of the advancing substrate 106 is between the slot opening 114 of the slot die applicator 104 and an advancing pattern surface 126. Because the minimum distance, Hg, between the pattern surface 126 of the pattern element 122 and the first lip 116 and the second lip 118 is less than the unconstrained caliper, Hs, of the substrate 106, a portion 106b of substrate 106 between the pattern surface 126 and the first lip 116 and second lip 118 of the slot die applicator 104 is compressed. The fluid 130 being discharged from the slot opening 114 is shown in FIG. 5C as being transferred to the second surface 110 of the substrate as the pattern surface 126 and adjacent compressed portion 106b of the substrate 106 advance past the slot opening 114.

Figure 5D:
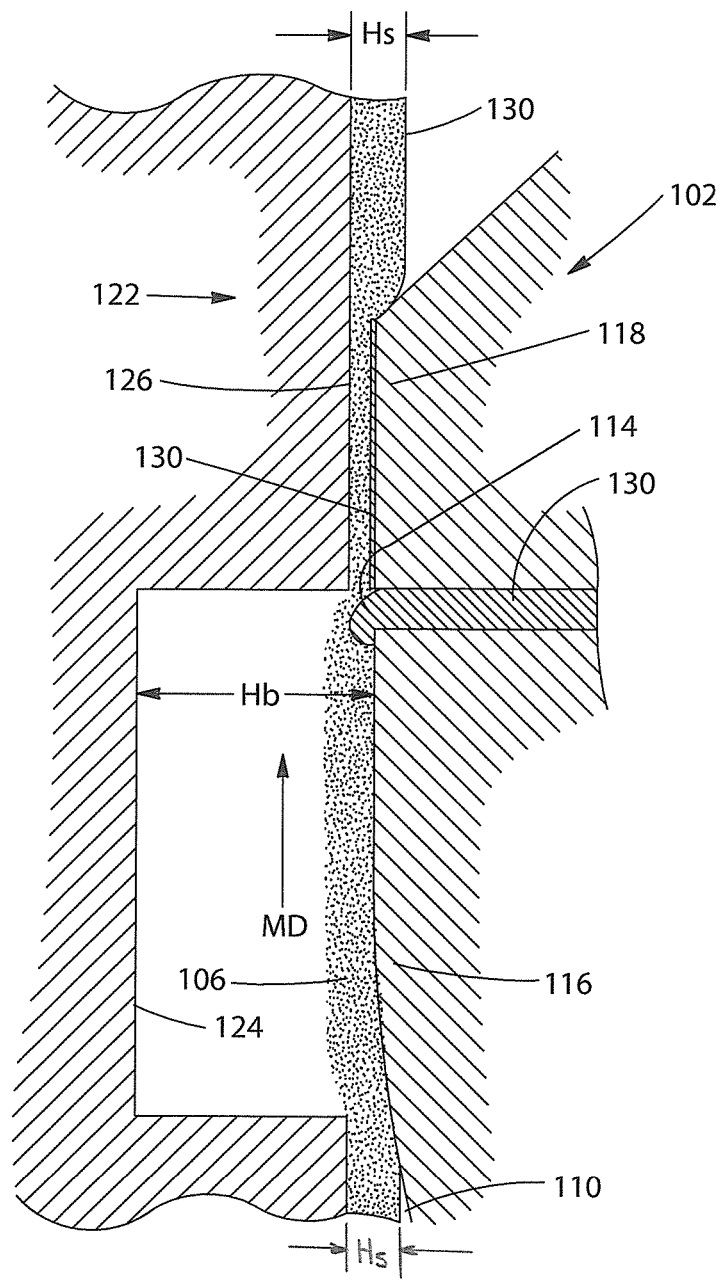
FIG. 5D is a detailed cross-sectional view of the substrate carrier and substrate of FIG. 5C wherein the pattern surface has advanced past the slot opening of the slot die applicator.

FIG. 5D is a detailed cross-sectional view of the substrate carrier 104 and substrate 106 of FIG. 5C wherein the pattern surface 126 has advanced past the slot opening 114 of the slot die applicator 104. As such, a portion 106b of the advancing substrate 106 is between the slot opening 114 of the slot die applicator 104 and an advancing base surface 124. Because the minimum distance, Hb, between the base surface 124 and the first lip 116 and the second lip 118 that is greater than the unconstrained caliper, Hs, of the substrate, a portion of substrate 106 between the base surface 124, slot opening 114, and the first lip 116 of the slot die applicator 104 is uncompressed. As such, the fluid 130 being discharged from the slot opening 114 is shown in FIG. 5D as ceasing to be transferred to the second surface 110 of the substrate 106 as the base surface 124 and adjacent uncompressed portion of the substrate advance past the slot opening 114.

Figure 6:
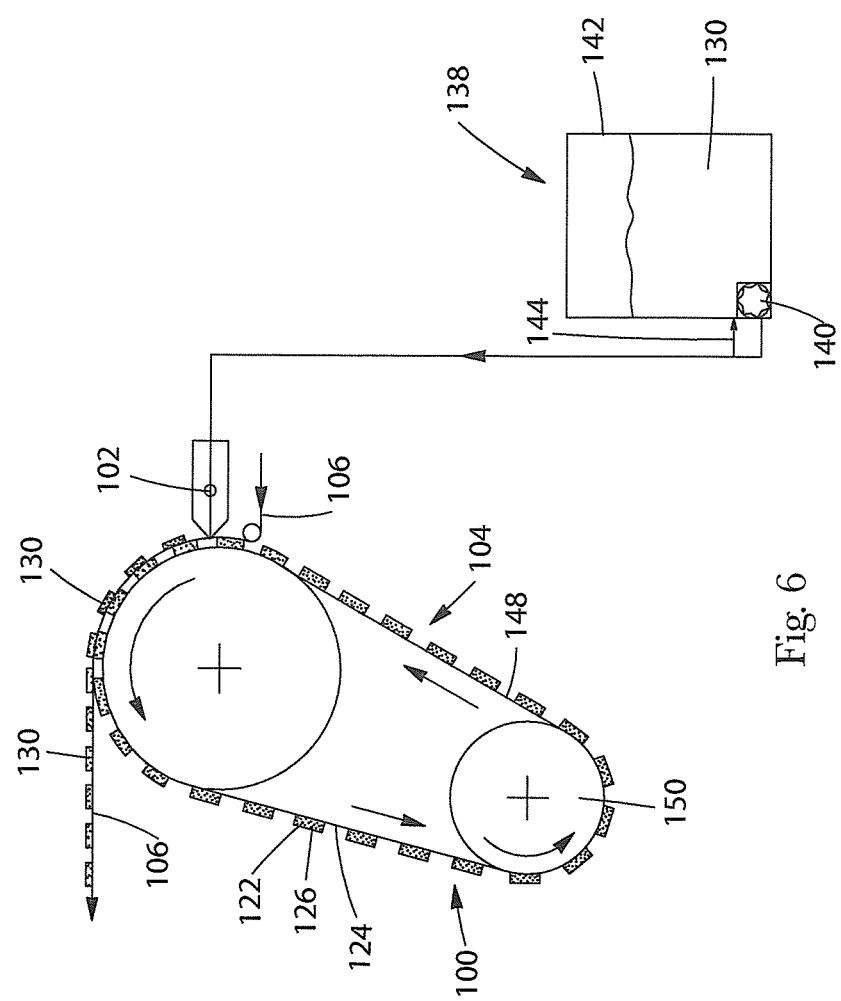
FIG. 6 is a schematic cross-sectional side view of an embodiment of a fluid application apparatus with a substrate carrier including a pattern belt.
Figure 7:
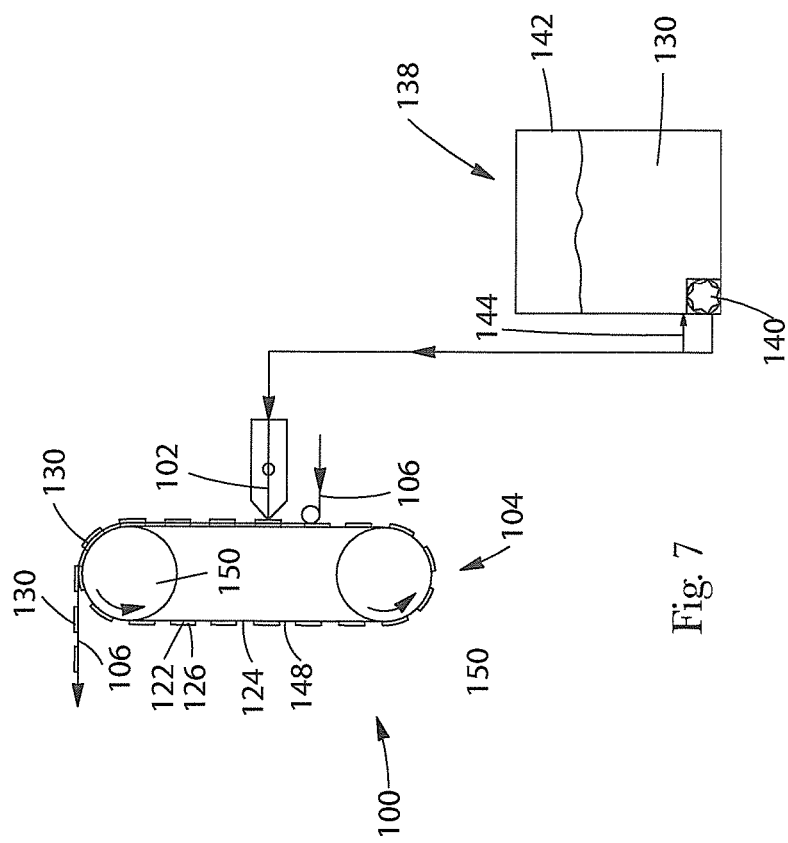
FIG. 7 is a schematic cross-sectional side view of another embodiment of a fluid application apparatus with a substrate carrier including a pattern belt.
Figure 8:
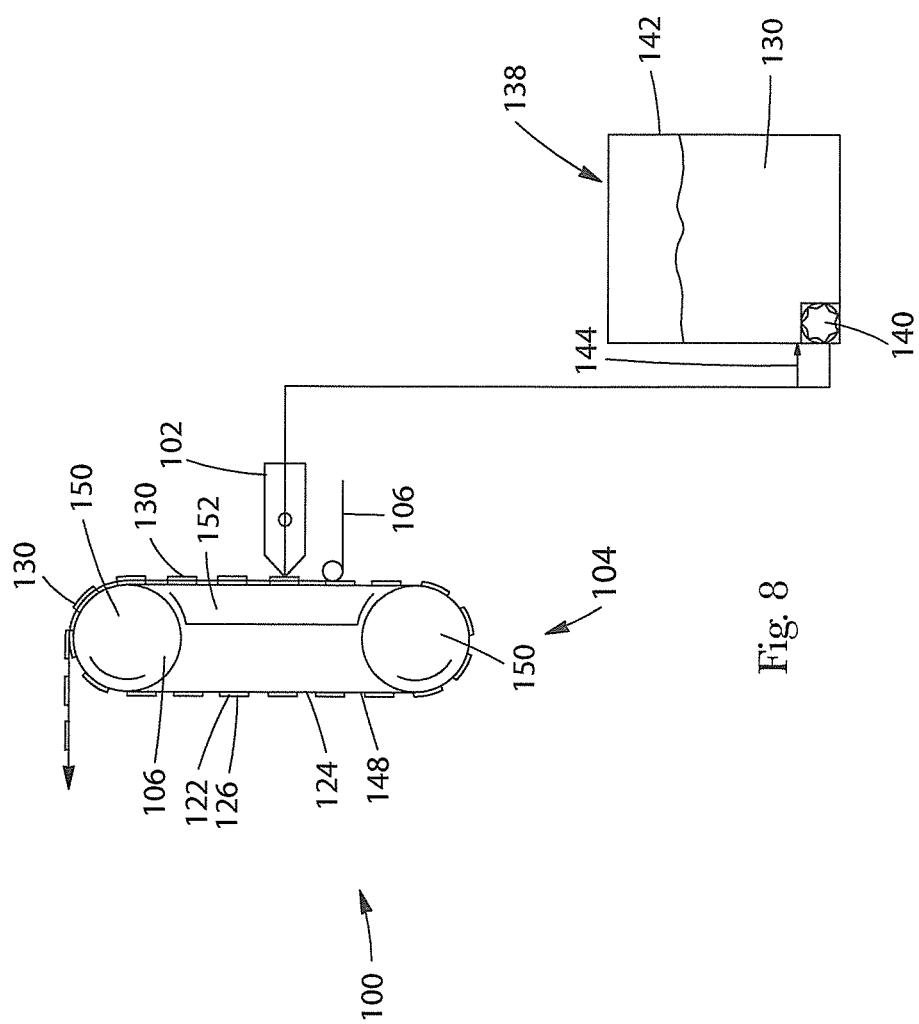
FIG. 8 is a schematic cross-sectional side view of another embodiment of a fluid application apparatus with a substrate carrier including a pattern belt and a backup plate.

As previously mentioned, various forms and configurations of substrate carriers may be used with the presently disclosed methods and apparatuses. For example, FIG. 6 shows a schematic cross-sectional side view of an embodiment of a fluid application apparatus 100 with a substrate carrier 104 including an endless pattern belt 148. The pattern belt 148 is wrapped around two rollers 150 adapted to advance pattern belt 148 and substrate past the slot die applicator 102. The pattern belt 148 may include various different combinations, shapes, and types of pattern elements 122 and base surfaces 124 and/or holes 136 as previous described. As shown in FIG. 6, the slot die applicator 102 is adjacent the pattern belt 148 at a location where the pattern belt 148 is partially wrapped around one of the rollers 150. It is to be appreciated that the slot die applicator 102 may be located adjacent other locations of the pattern belt 148. For example, FIG. 7 shows a schematic cross-sectional side view of an embodiment of a fluid application apparatus 100 wherein the slot die applicator 102 is adjacent the pattern belt 148 at a location between the rollers 150. And FIG. 8 shows a schematic cross-sectional side view of the embodiment of FIG. 7 with a backup plate 152 located behind the pattern belt 148, wherein the backup plate 148 provides support to the pattern belt 148 to help prevent the pattern belt from deflecting away from the slot die applicator 102.

With reference to the above description and associated figures, it is to be appreciated that the apparatuses 100 herein may be used to apply adhesive 130 discharged from a slot die applicator 102 to a substrate 106 in a pattern by continuously advancing the substrate in a machine direction past a first lip 116, second lip 118, and slot opening 114 in the slot die applicator 102. The substrate 106 may be engaged with a substrate carrier 104 that may include a base surface 124 and a pattern element 122, wherein the pattern element includes a pattern surface 126. The pattern element 122 protrudes from the base surface 124 to define a distance, Hp, between the pattern surface 126 and the base surface 124. As previously mentioned, in some embodiments, the substrate carrier may include holes 136 instead of or in combination with base surfaces 126 adjacent the pattern element 122. The substrate carrier 104 is positioned adjacent the slot die applicator 102 to define a minimum distance, Hg, between the pattern surface 126 of the pattern element 122 and the first lip 116 and the second lip 118 that is less than the unconstrained caliper, Hs, of the substrate 106. The second surface 110 of the substrate 106 may be advanced past the slot die applicator 102 while the first surface 108 of the substrate 106 is disposed on the substrate carrier 104. And the substrate 106 is intermittently compressed between the slot die applicator 102 and the pattern surface 126 of the pattern element 122 by advancing the pattern element as the pattern surface of the pattern element advances past the first lip 116, the slot opening 114, and the second lip 118 of the slot die applicator 102 while the first surface 108 of the substrate 106 is disposed on the substrate carrier 104.

Figure 9:
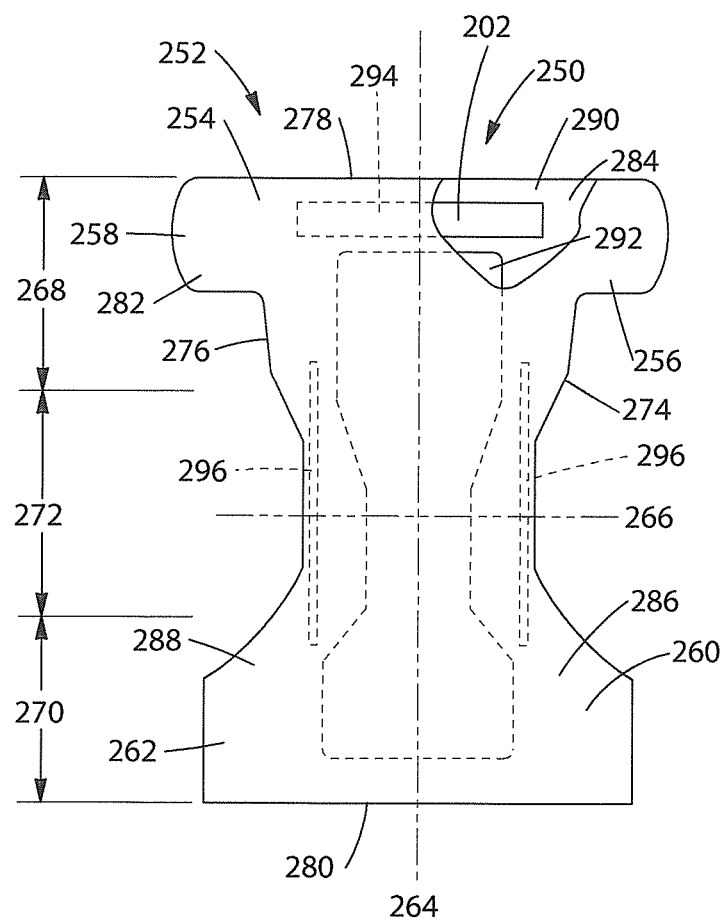
FIG. 9 is a top plan view of a disposable absorbent article.

As previously mentioned, the apparatuses 100 and methods herein may be used to provide for the application of adhesives in patterns to substrates and components during the manufacture of various different products. For the purposes of a specific illustration, FIG. 9 shows one example of a disposable absorbent article 250, such as described in U.S. Patent Publication No. US2008/0132865 A1, in the form of a diaper 252 that may be constructed from such substrates and components manipulated during manufacture according to the apparatuses and methods disclosed herein. In particular, FIG. 9 is a plan view of one embodiment of a diaper 252 including a chassis 254 shown in a flat, unfolded condition, with the portion of the diaper 252 that faces a wearer oriented towards the viewer. A portion of the chassis structure is cut-away in FIG. 9 to more clearly show the construction of and various features that may be included in embodiments of the diaper.

As shown in FIG. 9, the diaper 252 includes a chassis 254 having a first ear 256, a second ear 258, a third ear 260, and a fourth ear 262. To provide a frame of reference for the present discussion, the chassis is shown with a longitudinal axis 264 and a lateral axis 266. The chassis 254 is shown as having a first waist region 268, a second waist region 270, and a crotch region 272 disposed intermediate the first and second waist regions. The periphery of the diaper is defined by a pair of longitudinally extending side edges 274, 276; a first outer edge 278 extending laterally adjacent the first waist region 268; and a second outer edge 280 extending laterally adjacent the second waist region 270. As shown in FIG. 9, the chassis 254 includes an inner, body-facing surface 282, and an outer, garment-facing surface 284. A portion of the chassis structure is cut-away in FIG. 9 to more clearly show the construction of and various features that may be included in the diaper. As shown in FIG. 9, the chassis 254 of the diaper 252 may include an outer covering layer 286 including a topsheet 288 and a backsheet 290. An absorbent core 292 may be disposed between a portion of the topsheet 288 and the backsheet 290. As discussed in more detail below, any one or more of the regions may be stretchable and may include an elastomeric material or laminate as described herein. As such, the diaper 252 may be configured to adapt to a specific wearer's anatomy upon application and to maintain coordination with the wearer's anatomy during wear.

The absorbent article may also include an elastic waist feature 202 shown in FIG. 9 in the form of a waist band 294 and may provide improved fit and waste containment. The elastic waist feature 202 may be configured to elastically expand and contract to dynamically fit the wearer's waist. The elastic waist feature 202 can be incorporated into the diaper in accordance with the methods discussed herein and may extend at least longitudinally outwardly from the absorbent core 292 and generally form at least a portion of the first and/or second outer edges 278, 280 of the diaper 252. In addition, the elastic waist feature may extend laterally to include the ears. While the elastic waist feature 202 or any constituent elements thereof may comprise one or more separate elements affixed to the diaper, the elastic waist feature may be constructed as an extension of other elements of the diaper, such as the backsheet 290, the topsheet 288, or both the backsheet and the topsheet. In addition, the elastic waist feature 202 may be disposed on the outer, garment-facing surface 284 of the chassis 240; the inner, body-facing surface 282; or between the inner and outer facing surfaces. The elastic waist feature 202 may be constructed in a number of different configurations including those described in U.S. Pat. No. 7,432,413; U.S. Patent Publication No. 2007/0142798; and U.S. Patent Publication No. 2007/0287983; all of which are hereby incorporated by reference herein.

As shown in FIG. 9, the diaper 252 may include leg cuffs 296 that may provide improved containment of liquids and other body exudates. In particular, elastic gasketing leg cuffs can provide a sealing effect around the wearer's thighs to prevent leakage. It is to be appreciated that when the diaper is worn, the leg cuffs may be placed in contact with the wearer's thighs, and the extent of that contact and contact pressure may be determined in part by the orientation of diaper on the body of the wearer. The leg cuffs 296 may be disposed in various ways on the diaper 202.

The diaper 252 may be provided in the form of a pant-type diaper or may alternatively be provided with a re-closable fastening system, which may include fastener elements in various locations to help secure the diaper in position on the wearer. For example, fastener elements may be located on the first and second ears and may be adapted to releasably connect with one or more corresponding fastening elements located in the second waist region. It is to be appreciated that various types of fastening elements may be used with the diaper.

In the context of the previous discussion, the apparatuses 100 and methods herein may be used to provide for the application adhesives in patterns to substrates and components during the manufacture of an absorbent article. For example, adhesives may be applied in various patterns to portions of any of the topsheet, backsheet, absorbent core, leg cuffs, waist feature, ears, and fastening elements during the manufacture of an absorbent article. In some instances, the adhesive may be a different color than that of the substrate.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
    a chassis comprising:
        an inner, body-facing surface;
        an outer, garment-facing surface;
        a first waist region;
        a second waist region; and
        a crotch region disposed intermediate the first and second waist regions; and
    a pair of longitudinally extending side edges;
    a first outer edge extending laterally adjacent the first waist region;
    a second outer edge extending laterally adjacent the second waist region;
    a substrate including a first surface disposed opposite of a second surface and an unconstrained caliper, Hs;
    adhesive discharged directly from a slot die applicator onto the second surface of the substrate in an area having a shape that is substantially the same as a shape defined by a pattern surface that is positioned a minimum distance, Hg, from the slot die applicator that is less than the unconstrained caliper, Hs, of the substrate; and
    wherein the substrate carrier further comprises a base surface, wherein a pattern element protrudes from the base surface to define a distance, Hp, between the pattern surface and the base surface such that a sum of the distance, Hp, and distance, Hq, is greater than the unconstrained caliper, Hs, of the substrate.

2. The absorbent article of claim 1, further comprising a backsheet, wherein the backsheet includes the substrate.

3. The absorbent article of claim 1, further comprising a backsheet, and wherein the substrate is a topsheet connected with the backsheet.

4. The absorbent article of claim 1, further comprising
    a topsheet;
    a backsheet connected with the topsheet;
    an absorbent core interposed between the backsheet and the topsheet; and
    wherein the absorbent core includes the substrate.

5. The absorbent article of claim 1, further comprising an elastic waist feature, wherein the elastic waist feature includes the substrate.

6. The absorbent article of claim 1, further comprising a leg cuff, wherein the leg cuff includes the substrate.

7. The absorbent article of claim 1, further comprising a fastening element, wherein the fastening element includes the substrate.

8. The absorbent article of claim 1, wherein the adhesive and the substrate are different colors.

9. The absorbent article of claim 1, wherein the substrate comprises a nonwoven.

\* \* \* \* \*